(12) United States Patent
Shao et al.

(10) Patent No.: US 11,426,144 B2
(45) Date of Patent: Aug. 30, 2022

(54) METHOD AND DEVICE FOR ELASTICITY DETECTION

(71) Applicant: WUXI HISKY MEDICAL TECHNOLOGIES CO., LTD., Wuxi (CN)

(72) Inventors: Jinhua Shao, Wuxi (CN); Jin Sun, Wuxi (CN); Houli Duan, Wuxi (CN)

(73) Assignee: WUXI HISKY MEDICAL TECHNOLOGIES CO., LTD., Wuxi (CN)

(*) Notice: Subject to any disclaimer, the term of this patent is extended or adjusted under 35 U.S.C. 154(b) by 135 days.

(21) Appl. No.: 15/655,844

(22) Filed: Jul. 20, 2017

(65) Prior Publication Data

US 2017/0311929 A1    Nov. 2, 2017

Related U.S. Application Data (63) Continuation of application No. PCT/CN2016/103485, filed on Oct. 27, 2016.

(30) Foreign Application Priority Data

Oct. 29, 2015 (CN) .......................... 201510718719.3

(51) Int. Cl.
    *A61B 8/08* (2006.01)
    *G01S 7/52* (2006.01)
    *A61B 8/00* (2006.01)

(52) U.S. Cl.
    CPC ............ *A61B 8/485* (2013.01); *A61B 8/5223* (2013.01); *A61B 8/54* (2013.01); *G01S 7/52042* (2013.01); *A61B 8/08* (2013.01); *A61B 8/5207* (2013.01)

(58) Field of Classification Search
    None
    See application file for complete search history.

(56) References Cited

U.S. PATENT DOCUMENTS 5,606,971 A *  3/1997  Sarvazyan ............... A61B 8/08
                                                    600/438
5,955,671 A    9/1999  Gilmore et al. ................. 73/597
                        (Continued)

FOREIGN PATENT DOCUMENTS

CN      101699280 A    4/2010
CN      104380134 A    2/2015
                        (Continued)

OTHER PUBLICATIONS

Publisher: IT'IS Foundation; Title: Tissue Properties Database V1.0; Release Date: Sep. 26, 2011; << https://itis.swiss/virtual-population/tissue-properties/database/density/ >> ; 3 pages total. (Year: 2011).*

(Continued)

*Primary Examiner* — James M Kish
(74) *Attorney, Agent, or Firm* — J.C. Patents (57) ABSTRACT

Disclosed are a method and a device for elasticity detection. The method comprises: controlling an excitation device (2) to periodically excite N shear waves in a tissue at a preset time interval and controlling an ultrasonic transducer (3) to transmit ultrasonic waves (101) to the tissue, where the excitation device and the ultrasonic transducer are maintained in contact with a surface of the tissue; receiving, by the ultrasonic transducer (3), an ultrasonic echo signal (102) corresponding to each of the shear waves; acquiring a propagation characteristic parameter (103) of each of the shear waves according to the ultrasonic echo signal corresponding to each of the shear waves; calculating an elasticity parameter of the tissue (104) according to propagation (Continued)

characteristic parameters of the N shear waves and a tissue density of the tissue.

5 Claims, 4 Drawing Sheets

(56) References Cited

U.S. PATENT DOCUMENTS

| | | | | |
|---|---|---|---|---|
| 2007/0049824 | A1* | 3/2007 | Konofagou | G01S 7/52042 600/437 |
| 2009/0056453 | A1* | 3/2009 | McAleavey | A61B 8/08 73/597 |
| 2011/0040185 | A1* | 2/2011 | Matsumura | A61B 8/00 600/443 |
| 2011/0319756 | A1 | 12/2011 | Zheng et al. | 600/438 |
| 2012/0108968 | A1* | 5/2012 | Freiburger | A61B 8/0825 600/443 |
| 2012/0278005 | A1* | 11/2012 | Sumi | A61B 5/0053 702/43 |
| 2013/0245442 | A1* | 9/2013 | Hazard | G01S 7/52036 600/438 |
| 2013/0317361 | A1* | 11/2013 | Tabaru | A61B 8/42 600/438 |
| 2013/0317362 | A1 | 11/2013 | Shi et al. | 600/438 |
| 2015/0173718 | A1* | 6/2015 | Tabaru | A61B 8/08 600/438 |
| 2015/0374338 | A1* | 12/2015 | Sandrin | A61B 8/485 600/438 |

FOREIGN PATENT DOCUMENTS

| | | |
|---|---|---|
| CN | 104825195 A | 8/2015 |
| CN | 105212968 A | 1/2016 |
| CN | 105662473 A | 6/2016 |
| JP | 2005-283265 | 10/2005 |
| JP | 2005-283265 A | 10/2005 |
| JP | 2009201989 | 9/2009 |
| JP | 2015-023913 A | 2/2015 |
| JP | 2016-506846 A | 3/2016 |
| RU | 2012 105 462 A | 8/2013 |
| WO | WO2011004661 | 1/2011 |
| WO | 2014128182 A1 | 8/2014 |
| WO | 2015029651 A1 | 3/2015 |
| WO | WO 2015/116893 A1 | 8/2015 |

OTHER PUBLICATIONS

Nevo et al., "Automated Tracking of the Mitral Valve Annulus Motion in Apical Echocardiographic Images Using Multidimensional Dynamic Programming", Ultrasound in Med. & Biol., vol. 33, No. 9, 2007, pp. 1389-1399 (Year: 2007).*

Ning, Minghao. "SIFT (Scale-invariant feature transform)". Towards Data Science, Apr. 9, 2019, pp. 1-23. << https://towardsdatascience.com/sift-scale-invariant-feature-transform-c7233dc60f37 >> (Year: 2019).*

The Chinese First Examination Report of corresponding Chinese application No. 201510718719.3, dated Aug. 30, 2017.

The Chinese Second Examination Report of corresponding Chinese application No. 201510718719.3, dated Apr. 13, 2018.

The extended European Search Report of corresponding European patent application No. 16859040.4-1124/3369382, dated Nov. 18, 2018.

The Japanese Examination Report of corresponding Japanese application No. 2018-540201, dated Mar. 13, 2019.

The Russian Examination Report of corresponding Russian Federation Application No. 2018119513/14(030693), dated Jan. 17, 2019.

The Chinese First Examination Report of corresponding China patent application No. 201510718719.3, dated Aug. 30, 2017.

International Search Report of corresponding International PCT Application No. PCT/CN2016/103485, dated Dec. 28, 2016.

Office Action of the corresponding Japan application.

* cited by examiner

METHOD AND DEVICE FOR ELASTICITY DETECTION

CROSS-REFERENCE TO RELATED APPLICATIONS

This application is a continuation of International Application No. PCT/CN2016/103485, filed on Oct. 27, 2016, which claims the priority benefit of China Patent Application No. 201510718719.3, filed on Oct. 29, 2015. The contents of the above identified applications are incorporated herein by reference in their entireties.

TECHNICAL FIELD

The present invention relates to the technical field of medical instruments, in particularly to a method and a device for elasticity detection.

BACKGROUND

The elasticity of biological tissues is closely related to a characteristic of a lesion, thereby having important reference value for disease diagnosis. Therefore, the elasticity detection technique for non-destructive elasticity detection of viscoelastic medium such as human liver has been widely used in recent years.

Elasticity detection technique is used to quantitatively detect elasticity information of a tissue, i.e., elasticity modulus. The basic principle is that applying an internal (including its own) or an external dynamic/static/quasi-static excitation on a tissue, and under the action of elastic mechanics, biomechanics and other physical laws, the tissue will produce a response. Since different tissues (including normal and pathological tissues) have different elasticity coefficients (stress/strain), they have different strains after being subjected to an external force. The image transformation is performed on echo signals before and after tissue deformation, thereby visually displaying the elasticity of the tissue by the color of the image, and locating the lesion.

At present, in order to ensure that the elasticity detection results of the tissue are as accurate as possible, it is often necessary to repeat the tissue measurement several times to obtain a final elasticity detection result. That is, an operator places a probe in the corresponding position of the tissue, starts a first measurement, and controls the host for a related processing to obtain a first elasticity detection result; and then places the probe in the corresponding position of the tissue again and starts a second measurement to obtain a second elasticity detection result. The above process is repeated for times. A final elasticity detection result is obtained by considering multiple elasticity detection results obtained above.

In the above measurement, as the operator performs multiple measurements by using a hand-held probe, he needs to locate the measurement position for several times, so it is hard to ensure that the located measurement position for every time is the same position, leading a deviation of the measurement position, which affects accuracy of the measurement result.

SUMMARY

In order to solve at least one of the problems mentioned in the background, the present invention provides a method and a device for elasticity detection to overcome the drawback of the conventional multi-measurement method in which the elasticity detection result is poor in accuracy.

The present invention provides a method for elasticity detection, comprising:

step 1: maintaining an excitation device and an ultrasonic transducer in contact with a surface of a tissue; controlling the excitation device to periodically excite N shear waves in the tissue at a preset time interval, and controlling the ultrasonic transducer to transmit an ultrasonic wave to the tissue, N being an integer greater than 1;

step 2: receiving, by the ultrasonic transducer, an ultrasonic echo signal corresponding to each of the shear waves;

step 3: obtaining a propagation characteristic parameter of each of the shear waves according to the ultrasonic echo signal corresponding to each of the shear waves;

step 4: calculating obtaining an elasticity parameter of the tissue, according to the propagation characteristic parameters of the N shear waves and a tissue density of the tissue.

The present invention provides an elasticity detection device, comprising:

a control host, an excitation device and an ultrasonic transducer; the excitation device and the ultrasound transducer are maintained in contact with a surface of a tissue.

The control host comprises:

a controlling module, configured to control the excitation device to periodically excite N shear waves in the tissue at a preset time interval and, control the ultrasonic transducer to transmit an ultrasonic wave to the tissue, where N is an integer greater than 1;

a receiving module, configured to receive by the ultrasonic transducer an ultrasonic echo signal corresponding to each of the shear waves;

an acquiring module, configured to acquire a propagation characteristic parameter of each of the shear waves, according to an ultrasonic echo signal corresponding to each of the shear waves;

a calculating module, configured to calculate an elasticity parameter of the tissue, according to propagation characteristic parameters of the N shear waves and a tissue density of the tissue.

The present invention provides a method and a device for elasticity detection. When an elasticity detection of a tissue is required, the excitation device and the ultrasonic transducer are maintained in contact with the surface of the tissue, and the control host controls the excitation device to continuously and periodically excite N shear waves in the tissue at a preset time interval without manually locating the excitation device several times on the surface of the tissue, thereby ensuring that the N shear waves are excited in respect to the same position, which is helpful to ensure the accuracy of the final elasticity parameter detection result. After transmitting an ultrasonic wave corresponding to each of the shear waves and receiving an ultrasonic echo signal corresponding to each of the shear waves, by the ultrasonic transducer, a propagation characteristic parameter of each of the shear waves are acquired according to the ultrasonic echo signal corresponding to each of the shear waves. Finally, the elasticity parameter of the tissue is calculated according to the propagation characteristic parameter of the N shear waves and the density of the tissue. Since the excitation device and the ultrasonic transducer are maintained in contact with the surface of the tissue, the receiving of the ultrasonic echo signal is continuous, and thereby the elasticity detection efficiency can be improved.

DETAILED DESCRIPTION

Figure 1:
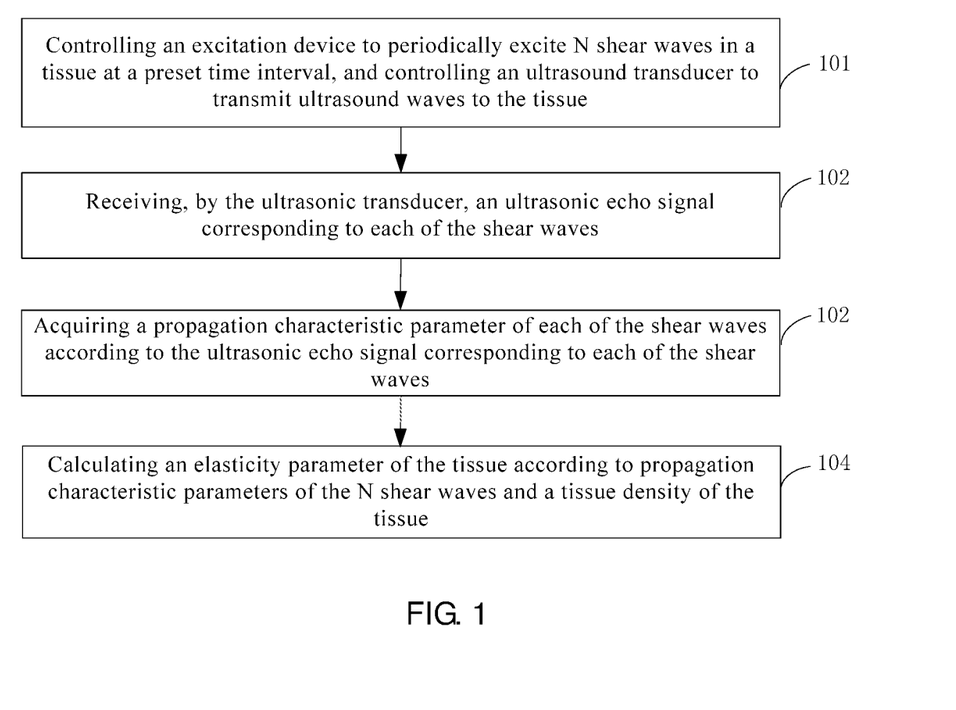
FIG. 1 is a flow chart of a first embodiment of an elasticity detection method of the present invention.

FIG. 1 is a flow chart of a first embodiment of an elasticity detection method of the present invention. In the present embodiment, the elasticity detection method is executed by an elasticity detection device, and the elasticity detection device includes a control host, an excitation device, an ultrasonic transducer, etc., wherein the excitation device and the ultrasonic transducer can be integrated in an elasticity detection probe, so that the elasticity detection method can be performed by the control host in the elasticity detection device, as shown in FIG. 1, the elasticity detection method includes:

step 101: controlling an excitation device to periodically excite N shear waves in a tissue at a preset time interval, and controlling an ultrasound transducer to transmit an ultrasound wave to the tissue.

Wherein the excitation device and the ultrasonic transducer are maintained in contact with a surface of the tissue, and N is an integer greater than 1.

In the present embodiment, when an elasticity detection of the tissue is required, the excitation device and the ultrasonic transducer are placed on the surface of the tissue, and are maintained in contact with the surface of the tissue.

Further, the control host controls the excitation device to periodically excite shear waves that will propagate in the tissue, at a preset time interval. After excitation of each of the shear waves, the ultrasonic transducer is controlled to transmit ultrasonic waves corresponding to the shear waves and receive corresponding ultrasonic echo signals for analyzing the propagation characteristics of the shear waves in the tissue.

In the present embodiment, the excitation device of the shear waves includes any one of a vibrator, an ultrasonic transducer, and a loudspeaker.

Correspondingly, an excitation mode of the shear waves may be that the vibrator applies a low frequency instantaneous vibration to an outer surface of the tissue so as to produce a shear wave in the tissue; an ultrasonic wave transmitted by the ultrasonic transducer focuses inside the tissue to generate an acoustic radiation force so as to produce shear waves in the tissue; and the loudspeaker generates sound waves with a certain frequency on an outer surface of the tissue so as to produce shear waves in the tissue.

It should be noted that in the mode in which a shear wave is generated by the ultrasonic transducer, the ultrasonic transducer for generating the shear wave and the ultrasonic transducer for transmitting an ultrasonic wave and receiving an ultrasonic echo signal can be the same or different.

Step 102: receiving, by the ultrasonic transducer, an ultrasonic echo signal corresponding to each of the shear waves.

The ultrasonic transducer transmits the received ultrasonic echo signal corresponding to each of the shear waves to a main control host, thereby allowing the control host to perform subsequent processing on each of the ultrasonic echo signals.

Step 103: acquiring a propagation characteristic parameter of each of the shear waves, according to the ultrasonic echo signal corresponding to each of the shear waves.

Step 104: calculating an elasticity parameter of the tissue, according to propagation characteristic parameters of the N shear waves and a tissue density of the tissue.

In the present embodiment, after receiving the ultrasonic echo signal corresponding to each of the shear waves, the control host can perform analysis and processing on each ultrasonic echo signal to obtain a propagation characteristic parameter corresponding to each of the shear waves, and then elasticity parameters of the tissue are acquired according to the propagation characteristic parameter of each of the shear waves.

Specifically, the control host can acquire a tissue motion parameter corresponding to each of the shear waves by performing signal processing on the ultrasonic echo signal corresponding to each of the shear waves, and then the propagation characteristic parameter of each of the shear waves is acquired according to the tissue motion parameter corresponding to each of the shear waves.

Wherein the signal processing on each ultrasonic echo signal includes at least one of the following: time-domain cross-correlation, spectral cross-correlation, square error sum, spot tracking, scale invariant feature point tracking, dynamic programming, zero cross-tracking, and peak searching. The tissue motion parameter corresponding to each of the shear waves, such as displacement or strain, can be acquired through signal processing on each ultrasonic echo signal. Thus, the propagation characteristic parameter corresponding to each of the shear waves, such as propagation speed or propagation attenuation coefficient, can be acquired based on the tissue motion parameter.

After the acquirement of the propagation characteristic parameter of each of the shear waves, the elasticity parameter of the tissue can be calculated according to the propagation characteristic parameter of each of the shear waves and the tissue density of the tissue. The elasticity parameter includes at least one of the following parameters: shear modulus, Young's modulus, shear elasticity, shear viscosity, mechanical impedance, mechanical relaxation time and anisotropy, wherein in general the shear modulus or the Young's modulus is mainly acquired.

In the present embodiment, since the excitation device and the ultrasonic transducer are always maintained in contact with a surface of the tissue during the process of f multiple elasticity detections of the tissue, and start of multiple detection processes by using the excitation device and the ultrasonic transducer are controlled by the control host, there is no need for the operator to relocate the position of the excitation device and the ultrasonic transducer on the surface of the tissue when starting the elasticity detection process every time. Furthermore, the control host can continuously receive ultrasonic echo signals received by the ultrasonic transducer during each elasticity detection process, and after receiving the ultrasonic echo signal corresponding to the each of the shear waves, that is the multiple elasticity detection processes, the control host performs concentration process on the ultrasonic echo signals so as to acquire the propagation characteristic parameter corresponding to each of the shear waves. Finally the elasticity detection results of the tissue, i.e., the elasticity parameters, are acquired according to the propagation characteristic parameter corresponding to each of the shear waves and the tissue density.

Figure 2:
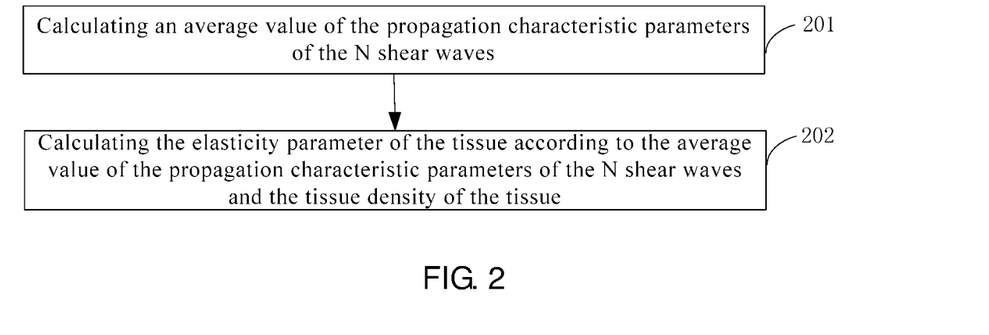
FIG. 2 is a flow chart of one concrete implementation of step 104 of the embodiment shown in FIG. 1.
Figure 3:
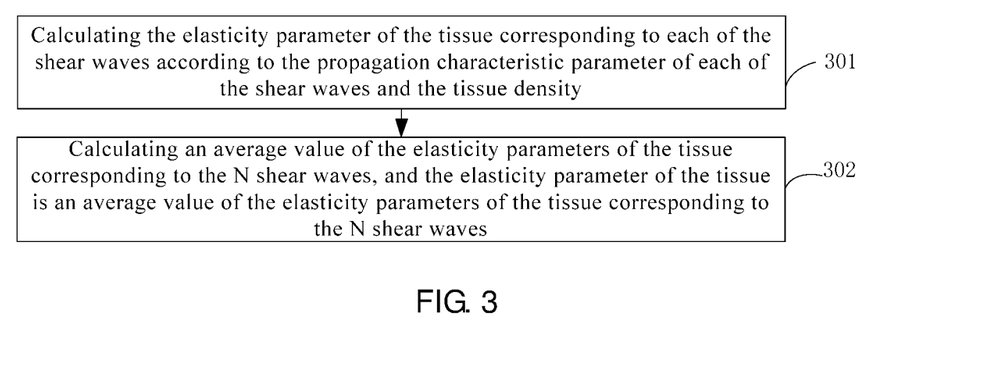
FIG. 3 is a flow chart of another concrete implementation of step 104 of the embodiment shown in FIG. 1.

Specifically, the control host can calculate the elasticity parameter of the tissue, according to the propagation characteristic parameters of the N shear waves and the tissue density of the tissue, in two alternative ways as shown in FIGS. 2 and 3.

FIG. 2 is a flow chart of one concrete implementation of step 104 of the embodiment shown in FIG. 1, as shown in FIG. 2, including the following steps:

step 201: calculating an average value of the propagation characteristic parameters of the N shear waves; and step 202: calculating an elasticity parameter of the tissue according to the average value of the propagation characteristic parameters of the N shear waves and the tissue density.

In the present embodiment, it is possible to first calculate an average value of the propagation characteristic parameters, such as displacements, of the N shear waves, and then a correlation calculation is performed based on the average value and the tissue density, to obtain the elasticity parameters of the tissue, such as elasticity modulus and Young's modulus.

FIG. 3 is a flow chart of another concrete implementation of step 104 of the embodiment shown in FIG. 1, as shown in FIG. 2, including the following steps:

step 301: calculating the elasticity parameter of the tissue corresponding to each of the shear waves, according to the propagation characteristic parameter of each of the shear waves and the tissue density;

step 302: calculating an average value of elasticity parameters of the tissue respectively corresponding to the N shear waves, and the elasticity parameter of the tissue is an average value of the elasticity parameters of the tissue respectively corresponding to the N shear waves.

In the present embodiment, it is possible to first calculate the elasticity parameter of the tissue corresponding to each shear wave, that is every elasticity detection process, and then an average value of the N elasticity parameters may be calculated, and this average value may be used as the final elasticity parameter of the tissue.

In the above embodiment, when an elasticity detection of the tissue is required, the excitation device and the ultrasonic transducer are maintained in contact with the surface of the tissue, and the control host controls the excitation device to continuously and periodically excite N shear waves in the tissue at a preset time interval without manually locating the excitation device several times on the surface of the tissue, thereby ensuring that the N shear waves are excited in respect to the same position, which is helpful to ensure accuracy of the final elasticity parameter detection result. After transmitting the ultrasonic wave corresponding to each of the shear waves and receiving the ultrasonic echo signal corresponding to each of the shear waves by the ultrasonic transducer, the propagation characteristic parameter of each of the shear waves is acquired according to the ultrasonic echo signal corresponding to each of the shear waves. Finally, an elasticity parameter of the tissue is calculated according to propagation characteristic parameters of the N shear waves and the density of the tissue. Since the excitation device and the ultrasonic transducer are maintained in contact with the surface of the tissue, the receiving of the ultrasonic echo signals is continuous, and thereby elasticity detection efficiency can be improved.

Figure 4:
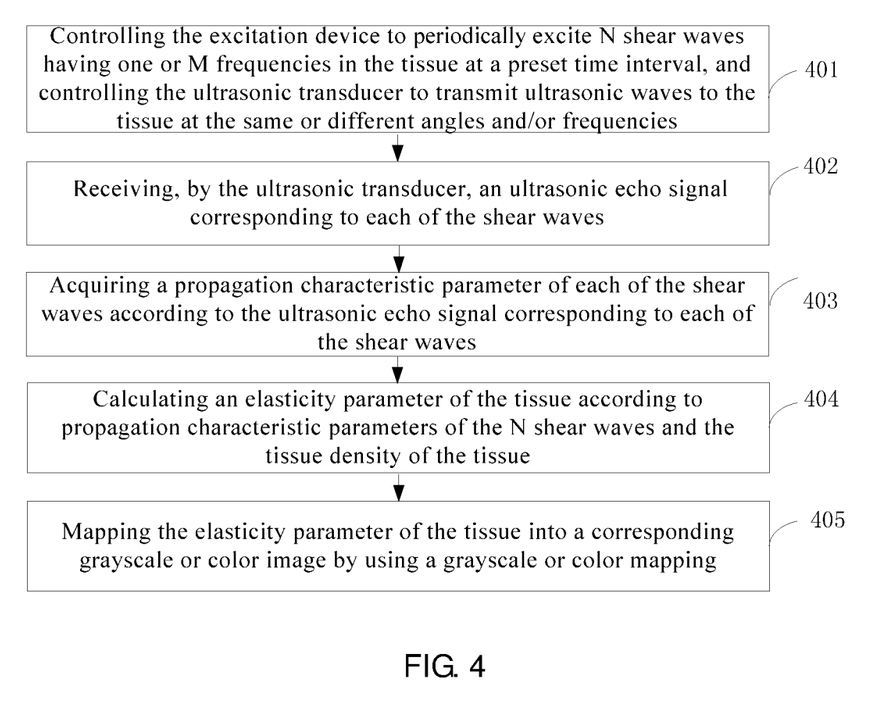
FIG. 4 is a flow chart of a second embodiment of the elasticity detection method of the present invention.

FIG. 4 is a flow chart of a second embodiment of the elasticity detection method of the present invention, and as shown in FIG. 4, the method includes the following steps:

step 401: controlling the excitation device to periodically excite N shear waves having one or M frequencies in the tissue at a preset time interval, and controlling the ultrasonic transducer to transmit ultrasonic waves to the tissue at the same or different angles and/or frequencies, wherein $2 \leq M \leq N$.

Wherein, $2 \leq M \leq N$.

In the present embodiment, in order to ensure a more accurate elasticity detection result of the tissue, frequencies of the N shear waves may be different, and further, the angles and frequencies of transmitting the ultrasonic waves and receiving the ultrasonic echo signals by the ultrasonic transducer can be different.

For example, in a mode in which a vibrator excites a shear wave, it is possible to control the vibrator to transmit mechanical vibrations with different frequencies, so that shear waves with different frequencies can be excited in the tissue. For another example, when exciting the shear waves by a loudspeaker, the loudspeaker can be controlled to transmit sound waves with different frequencies, thereby exciting the shear waves with different frequencies.

It should be noted that the control of each of the shear waves and the control of the ultrasound waves may include any one of the following combinations: exciting the shear waves with a single frequency, and transmitting the ultrasonic waves with the same frequency to the tissue at the same or different angles; exciting the shear waves with a single frequency, and transmitting the ultrasonic waves with different frequencies to the tissue at the same angle; exciting the shear waves with M frequencies, and transmitting the ultrasonic waves to the tissue at the same angle or frequency; and exciting the shear waves with M frequencies, and transmitting the ultrasonic waves to the tissue at different angles or frequencies or at different angles and frequencies, and so on.

In the present embodiment, by controlling the excitation device and the ultrasonic transducer to generate the shear waves with different frequencies and the ultrasonic waves with different angles in the tissue, elasticity detection dimension of the tissue is diversified, which is helpful to improve accuracy and reliability of the detection results.

Step 402: receiving, by the ultrasonic transducer, an ultrasonic echo signal corresponding to each of the shear waves.

Step 403: acquiring the propagation characteristic parameter of each of the shear waves according to the ultrasonic echo signal corresponding to each of the shear waves.

Step 404: calculating the elasticity parameter of the tissue according to propagation characteristic parameters of the N shear waves and the tissue density of the tissue.

Step 405: mapping the elasticity parameter of the tissue into a corresponding grayscale or color image by using a grayscale or color mapping.

In the present embodiment, in order to more intuitively understand the elasticity status of the tissue, the calculated elasticity parameter can be mapped in color to obtain a corresponding elasticity image.

Figure 5:
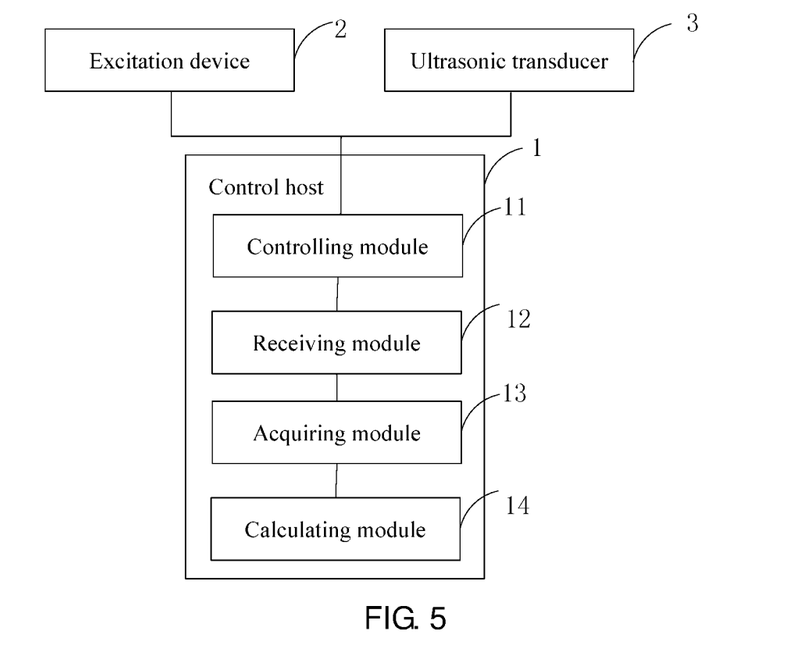
FIG. 5 is a schematic diagram of a first embodiment of an elasticity detection device of the present invention.

FIG. 5 is a schematic diagram of a first embodiment of an elasticity detection device of the present invention, and as shown in FIG. 5, the elasticity detection device includes:

a control host 1, an excitation device 2 and an ultrasonic transducer 3.

The control host 1 includes a controlling module 11, a receiving module 12, an acquiring module 13, and a calculating module 14.

The controlling module 11 is configured to control the excitation device to periodically excite N shear waves in a tissue at preset time interval and control the ultrasonic transducer to transmit an ultrasound wave to the tissue, wherein the excitation device and the ultrasonic transducer are maintained in contact with a surface of the tissue, and N is an integer greater than 1.

The receiving module 12 is configured to receive an ultrasonic echo signal corresponding to each of the shear waves by the ultrasonic transducer.

The acquiring module 13 is configured to acquire a propagation characteristic parameter of each of the shear waves according to the ultrasonic echo signal corresponding to each of the shear waves.

The calculating module 14 is configured to calculate an elasticity parameter of the tissue, according to propagation characteristic parameters of the N shear waves and the tissue density of the tissue.

The elasticity detection device of the present embodiment can be used in the technical solutions of the embodiments of the above-mentioned method, and has similar realization principle and technical effect thereto, and thus will not be repeated here.

It will be understood by those of ordinary skill in the art that all or part of the steps of the embodiments of the method described above may be accomplished by using program related hardware, and the program may be stored in a computer readable storage medium. When the program is executed, the steps included in the embodiments of the above-mentioned method will be executed. The above-mentioned storage medium includes various kinds of media that can store a program code, such as a ROM, a RAM, a magnetic disk, or an optical disk.

Finally, it should be noted that, the above embodiments are merely intended to illustrate rather than limit the technical solutions of the present invention; although the present invention has been described in detail with reference to the above embodiments, one with ordinary skill in the art shall understand that modifications can still be made to the technical solutions recorded in the foregoing embodiments, or equivalent substitutions can still be made to part or all of the technical features therein. Neither these modifications nor these substitutions shall make the essence of the corresponding technical solutions depart from the scope of the technical solutions in the above embodiments of the present application.

What is claimed is:

1. A method for elasticity detection, comprising:
    step 1: maintaining an excitation device and an ultrasonic transducer in contact with a surface of a tissue during N elasticity detections; controlling the excitation device to periodically excite N shear waves in the tissue at a preset time interval, wherein the N shear waves are continuously excited within the preset time interval without manually locating the excitation device several times on the surface of the tissue so as to ensure that the N shear waves are excited in respect to a same position, and controlling the ultrasonic transducer to transmit an ultrasonic wave to the tissue, wherein N is an integer greater than 1, and wherein the excitation device is the same as the ultrasonic transducer for transmitting the ultrasonic wave;
    step 2: receiving, by the ultrasonic transducer, an ultrasonic echo signal corresponding to each of the shear waves;
    step 3: obtaining a propagation characteristic parameter of each of the shear waves according to the ultrasonic echo signal corresponding to each of the shear waves;
    step 4: calculating elasticity parameters of the tissue according to propagation characteristic parameters of the N shear waves and according to a known tissue density of the tissue, wherein the elasticity parameters comprise mechanical impedance, mechanical relaxation time and anisotropy, and wherein the propagation characteristic parameters comprise a propagation attenuation coefficient;
    wherein the step 1 comprises:
    controlling the ultrasonic transducer to transmit ultrasonic waves to the tissue at different angles or different frequencies, wherein the N shear waves have different frequencies;
    wherein the step 4 comprises:
    calculating the elasticity parameters of the tissue corresponding to each of the shear waves according to the propagation characteristic parameter of each of the shear waves and according to the known tissue density; and
    calculating an average value of elasticity parameters of the tissue corresponding to the N shear waves as the elasticity parameters of the tissue;
    wherein the step 3 comprises:
    acquiring a tissue motion parameter corresponding to each of the shear waves by performing signal processing on the ultrasonic echo signal corresponding to each of the shear waves, wherein the signal processing comprises at least one of the following: spot tracking and zero cross-tracking; and
    acquiring a propagation characteristic parameter of each of the shear waves according to the tissue motion parameter corresponding to each of the shear waves;
    wherein after the step 4, the method further comprises:
    mapping the elasticity parameters of the tissue into a corresponding grayscale or color image by using a grayscale or color mapping to obtain an elasticity image.

2. The method according to claim 1, wherein the tissue motion parameter comprises a displacement or a strain.

3. The method according to claim 1, wherein the elasticity parameters further comprise at least one of following parameters: shear modulus, Young's modulus and shear elasticity, shear viscosity.

4. The method according to claim 1, wherein an excitation mode of the shear waves are that an ultrasonic wave transmitted by the ultrasonic transducer focuses inside the tissue to generate an acoustic radiation force so as to produce shear waves in the tissue.

5. A device for elasticity detection, comprising:
    a control host, an excitation device and an ultrasonic transducer; where the excitation device and the ultrasound transducer are maintained in contact with a surface of a tissue during N elasticity detections, wherein the excitation device is the same as the ultrasonic transducer for transmitting the ultrasonic wave; and
    the control host comprises a processor and a memory storing instructions thereon, the processor when executing the instructions, being configured to:
    control the excitation device to periodically excite N shear waves in the tissue at a preset time interval, wherein the N shear waves are continuously excited within the preset time interval without manually locating the excitation device several times on the surface of the tissue so as to ensure that the N shear waves are excited in respect to a same position and control the ultrasonic transducer to transmit ultrasonic waves to the tissue, N being an integer greater than 1;
    receive by the ultrasonic transducer an ultrasonic echo signal corresponding to each of the shear waves;

acquire a propagation characteristic parameter of each of the shear waves according to the ultrasonic echo signal corresponding to each of the shear waves; and calculate elasticity parameters of the tissue according to propagation characteristic parameters of the N shear waves and according to a known tissue density of the tissue, wherein the elasticity parameters comprise mechanical impedance, mechanical relaxation time and anisotropy, and wherein the propagation characteristic parameters comprise a propagation attenuation coefficient;

wherein the processor is specifically configured to control the ultrasonic transducer to transmit ultrasonic waves to the tissue at different angles or different frequencies, wherein the N shear waves have different frequencies;

wherein the processor is specifically configured to calculate the elasticity parameters of the tissue corresponding to each of the shear waves according to the propagation characteristic parameter of each of the shear waves and according to the known tissue density; and calculate an average value of elasticity parameters of the tissue corresponding to the N shear waves as the elasticity parameter of the tissue;

wherein the processor is specifically configured to acquire a tissue motion parameter corresponding to each of the shear waves by performing signal processing on the ultrasonic echo signal corresponding to each of the shear waves, wherein the signal processing comprises at least one of the following: spot tracking and zero cross-tracking; and acquire a propagation characteristic parameter of each of the shear waves according to the tissue motion parameter corresponding to each of the shear waves;

wherein the processor is specifically configured to map the elasticity parameters of the tissue into a corresponding grayscale or color image by using a grayscale or color mapping to obtain an elasticity image.

* * * * *